(12) United States Patent
Tak

(10) Patent No.: US 10,258,069 B2
(45) Date of Patent: *Apr. 16, 2019

(54) APPARATUS FOR STERILIZING FOOD OR MEDICAL APPLIANCE AND METHOD OF USING THE APPARATUS

(71) Applicant: Hyo Sung Tak, Busan (KR)

(72) Inventor: Hyo Sung Tak, Busan (KR)

(73) Assignee: Hyo Sung Tak, Busan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/678,475

(22) Filed: Aug. 16, 2017

(65) Prior Publication Data

US 2018/0332877 A1    Nov. 22, 2018

(30) Foreign Application Priority Data

May 18, 2017    (KR) .......................... 10-2017-0061374

(51) Int. Cl.
*A23L 23/00*    (2016.01)
*A61L 2/03*    (2006.01)
*A23L 3/32*    (2006.01)

(52) U.S. Cl.
CPC ................. *A23L 23/00* (2016.08); *A23L 3/32* (2013.01); *A61L 2/03* (2013.01); *A23V 2002/00* (2013.01); *A61L 2202/14* (2013.01); *A61L 2202/24* (2013.01)

(58) Field of Classification Search
CPC ..................................... A61L 2/03; A23L 3/32
See application file for complete search history.

(56) References Cited

U.S. PATENT DOCUMENTS 6,497,839 B1 * 12/2002 Hasegawa ................ A23B 9/06
422/186.03

FOREIGN PATENT DOCUMENTS

KR    10-0241368 B1    3/2000
KR    10-0543138 B1    4/2006

* cited by examiner

*Primary Examiner* — Sean E Conley
(74) *Attorney, Agent, or Firm* — Rabin & Berdo, P.C.

(57) ABSTRACT

Disclosed is an apparatus for sterilizing a food or a medical appliance. The apparatus includes a sterilization tank, electrode rods arranged to face each other at both sides of the bottom surface of the sterilization tank and made of a conductive metal selected from Pt, Au, Ag, Cu, Sn, and alloys thereof, the electrode rod at one side being connected to a positive (+) electrode and the electrode rod at the other side being connected to a negative (−) electrode, and a field effect transistor connected to the electrode rods through 2.0 to 5.0 mm thick electric wires. When electric power is applied to the electrode rods, a content in the sterilization tank is instantaneously sterilized by electrical energy. The apparatus can kill microbial bacteria by a physical process for instantaneous sterilization including applying electrical energy to an object in need of sterilization in a food or a medical appliance. Also disclosed is a method of using the apparatus.

6 Claims, 3 Drawing Sheets

Water Quality Test Report

1. Sample Information

| Sample Name | Water from water purifier | Received on | July 12, 2016 | Receipt No. | Application No. 472-2 |
|---|---|---|---|---|---|
| Use | For reference | Completed on | July 19, 2016 | Test method | Process test guideline for drinking water |
| Client | KO Hwa-ok, Lijin Co., Ltd., 202 Deokpo-ro Gwangdo-myeon, Tongyoung-si, Gyeongnam, Korea. | | | | |
| Sampled on | July 12, 2016 | Sampled at | 202 Deokpo-ri Gwangdo-myeon, Tongyoung-si, Gyeongnam, Korea | | |

2. Water Quality Test Result

| No. | Test item | Water quality criterion | Result | No. | Test item | Water quality criterion | Result |
|---|---|---|---|---|---|---|---|
| 1 | General bacteria | ≤ 100 CFU/mL | 0 | 30 | 1,2-Dibromo-3-chloropropane | ≤ 0.003 mg/L | - |
| 2 | Total coliform group | Undetected/100 mL | Undetected | 31 | 1,4-dioxane | ≤ 0.05 mg/L | - |
| 3 | Coliform bacteria/Fecal coliform group | Undetected/100 mL | Undetected | 32 | Free residual chlorine | ≤ 4.0 mg/L | - |
| 4 | Lead | ≤ 0.01 mg/L | - | 33 | Total trihalomethane | ≤ 0.1 mg/L | - |
| 5 | Fluorine | ≤ 1.5 mg/L | - | 34 | Chloroform | ≤ 0.08 mg/L | - |
| 6 | Arsenic | ≤ 0.01 mg/L | - | 35 | Bromodichloromethane | ≤ 0.03 mg/L | - |
| 7 | Selenium | ≤ 0.01 mg/L | - | 36 | Dibromodichloromethane | ≤ 0.1 mg/L | - |
| 8 | Mercury | ≤ 0.001 mg/L | - | 37 | Chloral hydrate | ≤ 0.03 mg/L | - |
| 9 | Cyanogen | ≤ 0.01 mg/L | - | 38 | Dibromoacetonitrile | ≤ 0.1 mg/L | - |
| 10 | Chromium | ≤ 0.05 mg/L | - | 39 | Dichloroacetonitrile | ≤ 0.09 mg/L | - |
| 11 | Ammonical nitrogen | ≤ 0.5 mg/L | - | 40 | Trichloroacetonitrile | ≤ 0.004 mg/L | - |
| 12 | Nitric nitrogen | ≤ 10 mg/L | - | 41 | Haloacetic acid | ≤ 0.1 mg/L | - |
| 13 | Cadmium | ≤ 0.005 mg/L | - | 42 | Formaldehyde | ≤ 0.5 mg/L | - |
| 14 | Boron | ≤ 1.0 mg/L | - | 43 | Hardness | ≤ 300 mg/L | - |
| 15 | Phenol | ≤ 0.005 mg/L | - | 44 | Potassium permanganate consumption | ≤ 10 mg/L | - |
| 16 | Diazinon | ≤ 0.02 mg/L | - | 45 | Odor | Odorless | - |
| 17 | Parathion | ≤ 0.06 mg/L | - | 46 | Taste | Tasteless | - |
| 18 | Fenitrothion | ≤ 0.04 mg/L | - | 47 | Copper | ≤ 1 mg/L | - |
| 19 | Carbaryl | ≤ 0.07 mg/L | - | 48 | Chromaticity | ≤ 5 degree | - |
| 20 | 1,1,1-trichloroethane | ≤ 0.1 mg/L | - | 49 | Detergent (anionic surfactants) | ≤ 0.5 mg/L | - |
| 21 | Tetrachloroethylene | ≤ 0.01 mg/L | - | 50 | Hydrogen ion concentration (pH) | 5.8-8.5 | - |
| 22 | Trichloroethylene | ≤ 0.03 mg/L | - | 51 | Zinc | ≤ 3 mg/L | - |
| 23 | Dichloromethane | ≤ 0.02 mg/L | - | 52 | Chlorine ion | ≤ 250 mg/L | - |
| 24 | Benzene | ≤ 0.01 mg/L | - | 53 | Evaporation residue | ≤ 500 mg/L | - |
| 25 | Toluene | ≤ 0.7 mg/L | - | 54 | Iron | ≤ 0.3 mg/L | - |
| 26 | Ethylbenzene | ≤ 0.3 mg/L | - | 55 | Manganese | ≤ 0.05 mg/L | - |
| 27 | Xylene | ≤ 0.5 mg/L | - | 56 | Turbidity | ≤ 0.5 NTU | - |
| 28 | 1,1-dichloroethylene | ≤ 0.03 mg/L | - | 57 | Sulfate ion | ≤ 200 mg/L | |
| 29 | Carbon tetrachloride | ≤ 0.002 mg/L | | 58 | Aluminum | ≤ 0.2 mg/L | |

| Judgement | Suitable as drinking water because the three water quality criteria were met |
|---|---|
| Items exceeding the criteria (unsuitable items) | - |
| Remarks | This test report is just for the above sample and shall not be used for other purposes, such as advertisement or publicity article, than what is stated herein |

July 19, 2016

Director of the Institute for Health and Environment, Gyeongsangnamdo, Korea

52732, West Office, Gyeongnam Provincial Government Building, 2026 Wallasan-ro Jinju-si Gyeongnam TEL: 055)254-2316 FAX: 055)254-2329

FIG. 4

APPARATUS FOR STERILIZING FOOD OR MEDICAL APPLIANCE AND METHOD OF USING THE APPARATUS

BACKGROUND OF THE INVENTION

1. Field of the Invention

The present invention relates to an apparatus for sterilizing a food material or a medical appliance to keep the food material or medical appliance in a clean and sanitary state, and a method of using the apparatus. More specifically, the present invention relates to a technology for sterilizing a food or a medical appliance in which when electric power is applied to an electrode rod connected to a positive (+) electrode and an electrode rod connected to a negative (−) electrode, which are connected to a field effect transistor through 2.0 to 5.0 mm thick electric wires and made of a special material on the bottom surface or wall surface of a sterilization tank, the food or medical appliance is instantaneously sterilized by electrical energy instantaneously generated in the sterilization tank, thus avoiding the need to use ultrasonic waves or ozone as in the prior art.

2. Description of the Related Art

Medical appliances refer to devices that are used to treat diseases. Inexpensive medical devices, such as syringes, syringe needles, and drip injection devices, are disposed of without being reused for the purpose of preventing hospital acquired bacterial and viral infections and other medical accidents and for economic reasons. On the other hand, surgical devices, such as laparoscopes, thoracoscopes, and arthroscopes, and other medical devices, such as endoscopes, are repeatedly reused due to their high prices.

Many approaches aimed at reusing expensive medical appliances have been proposed. For example, Korean Patent No. 10-0543138 discloses a method and apparatus for sterilizing and cleaning a medical device with high sterilizing activity in a short time without corroding metal. The method includes dissolving a halide salt consisting of a bromide compound and one or more other halide compounds in water to prepare an aqueous electrolyte solution, directly electrolyzing the electrolyte aqueous solution using electrodes consisting of a positive electrode and a negative electrode to produce electrolyzed water containing a hypohalogenous acid, and bringing the electrolyzed water into contact with an attachment of a medical device after use while maintaining the pH of the electrolyzed water at 6 or higher.

However, the use of the apparatus is avoided because the highly toxic halide compounds are difficult to handle/use. Time-consuming processes, such as aeration, are required to remove harmful components from chemicals remaining attached to the medical device after sterilization/cleaning, making it impossible to use the apparatus immediately after sterilization.

Further, Korean Patent No. 10-0241368 discloses an apparatus for sterilizing a food to keep the food in a clean state. The apparatus includes a UV lamp 9 provided inside a cover of a reservoir 1 adapted to temporarily store a food or a drink such that air in an inner space between a storage container and a cover 8 of the reservoir 1 is sterilized, an ozonizer 10 for generating ozone to directly sterilize the food or drink, and an aerator 21 immersed in the food or drink through a tube 19 connected to the ozonizer 10 to supply ozone generated from the ozonizer 10 to the food or drink. The UV lamp emits UV light at 184.9 nm and UV light at 253.7 nm, which are responsible for 12-32% and 63-88% of the total UV light, respectively.

In addition to these approaches, traditional sterilization and disinfection techniques have been widely used to control the sanitary conditions of medical appliances and foods, for example, by ultrasonic cleaning and subsequent disinfection with ethyl alcohol, a quaternary ammonium antiseptic, an iodine antiseptic or an aldehyde antiseptic, immersion in an antiseptic or disinfection in an atmosphere filled with formalin gas or ethylene oxide gas. However, these techniques require a long time for sterilization and deodorization and are unsuitable for frequent reuse. Further, these techniques require the use of complex cleaning apparatuses, incurring enormous cleaning costs, and involve disposal of waste cleaning water after sterilization.

SUMMARY OF THE INVENTION

The present invention has been made in view of the problems of the prior art, and is intended to provide novel sterilization means capable of effectively inhibiting the proliferation of bacteria in a sterilization tank or a food depot in an easy and safe manner, unlike conventional complicated apparatuses for sterilizing medical appliances or foods.

It is one object of the present invention to provide an apparatus for sterilizing a food or a medical appliance that can kill microbial bacteria by a physical process for instantaneous sterilization including applying electrical energy to an object in need of sterilization in a food or a medical appliance. It is another object of the present invention to provide a method of using the apparatus.

The present inventor has conducted research to develop a technology that can be applied to an apparatus for sterilizing/cleaning a food or a medical appliance.

One aspect of the present invention provides an apparatus for sterilizing/cleaning a food or a medical appliance including a sterilization/cleaning tank, electrode rods arranged to face each other at both sides of the bottom surface of the sterilization/cleaning tank and made of a conductive metal selected from Pt, Au, Ag, Cu, Sn, and alloys thereof, the electrode rod at one side being connected to a positive (+) electrode and the electrode rod at the other side being connected to a negative (−) electrode, and a field effect transistor connected to the electrode rods through 2.0 to 5.0 mm thick electric wires wherein when electric power is applied to the electrode rods, a solvent in the sterilization/cleaning tank is instantaneously sterilized by electrical energy to sterilize/clean the food or medical appliance.

The field effect transistor used in the sterilization/cleaning apparatus of the present invention may be selected from IGBT and MOSFET systems. The sterilization/cleaning apparatus of the present invention may further include a sensor and a control unit. The sensor is mounted in a connection unit of the apparatus or on the surface of the apparatus and the control unit is adapted to interrupt the internal power of the apparatus when the connection unit is disconnected or an external object approaches the surface of the apparatus, ensuring safety of the apparatus.

Another aspect of the present invention provides a method of using a sterilization/cleaning apparatus. The method of the present invention can be applied for practical use. For example, the method of the present invention may be used to sterilize a food or a medical appliance as an object in need of sterilization. Specifically, the method includes: constructing a sterilization/cleaning apparatus in which electrode rods made of a conductive metal selected from Pt, Au, Ag, Cu, Sn, and alloys thereof are arranged to face each other at both sides of the bottom surface of a sterilization/cleaning tank, the electrode rod at one side is connected to a positive (+) electrode, the electrode rod at the other side is connected to a negative (−) electrode, and a field effect transistor is connected to the electrode rods through 2.0 to 5.0 mm thick electric wires (step 1); and placing an object in need of sterilization in the sterilization tank and applying electric power to the electrode rods such that the object is instantaneously sterilized by electrical energy (step 2).

Specifically, the apparatus of the present invention can be applied to the sterilization of a meat broth for Korean traditional cold noodles or a soup for Korean traditional bean noodles. To this end, a meat broth for Korean traditional cold noodles or a soup for Korean traditional bean noodles is placed in the sterilization tank of the sterilization apparatus and electric power is intermittently applied to the electrode rods to generate electric energy, which can be used to block the proliferation of microbes in the meat broth or soup during storage. More preferably, the apparatus of the present invention further includes a sensor mounted inside the sterilization tank to detect the proliferation of microbes and a control unit. The sensor transmits the detected signals to the control unit. When microbes proliferate above a predetermined level, the control unit operates to apply electric power to the electrode rods.

Step 2 may be modified depending on the object to be sterilized. It should be understood that step 2 may be modified in such a manner that a solvent is placed in the sterilization tank instead of the object to be sterilized and electric power is applied to sterilize the solvent, which is used to sterilize a food or a medical appliance.

The present invention is effective in inhibiting the proliferation of bacteria in a conventional apparatus for sterilizing a medical container or a conventional food storage apparatus in an easy and safe manner.

The present invention is effective in inhibiting the proliferation of bacteria in water (solvent) stored in an apparatus for sterilizing a medical container or a food storage apparatus in an easy and safe manner by a physical process for instantaneous sterilization including applying electrical energy to the water to kill microbial bacteria.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 4 is an analytical report of water obtained from a water purifier to which an apparatus of the present invention is applied.

DETAILED DESCRIPTION OF THE INVENTION

Preferred embodiments of the present invention will now be described in detail with reference to the accompanying drawings in which an apparatus of the present invention is applied to the sterilization of a medical container or a liquid food storage apparatus.

However, the embodiments of the present invention are provided for illustrative purposes only and may be modified in different forms by adding technical features of the present invention to a conventional apparatus for sterilizing a medical container or a conventional liquid food storage apparatus. It is to be understood that similar modifications, equivalents, and substitutes that do not depart from the spirit and scope of the present invention are encompassed in the present invention.

Figure 1:
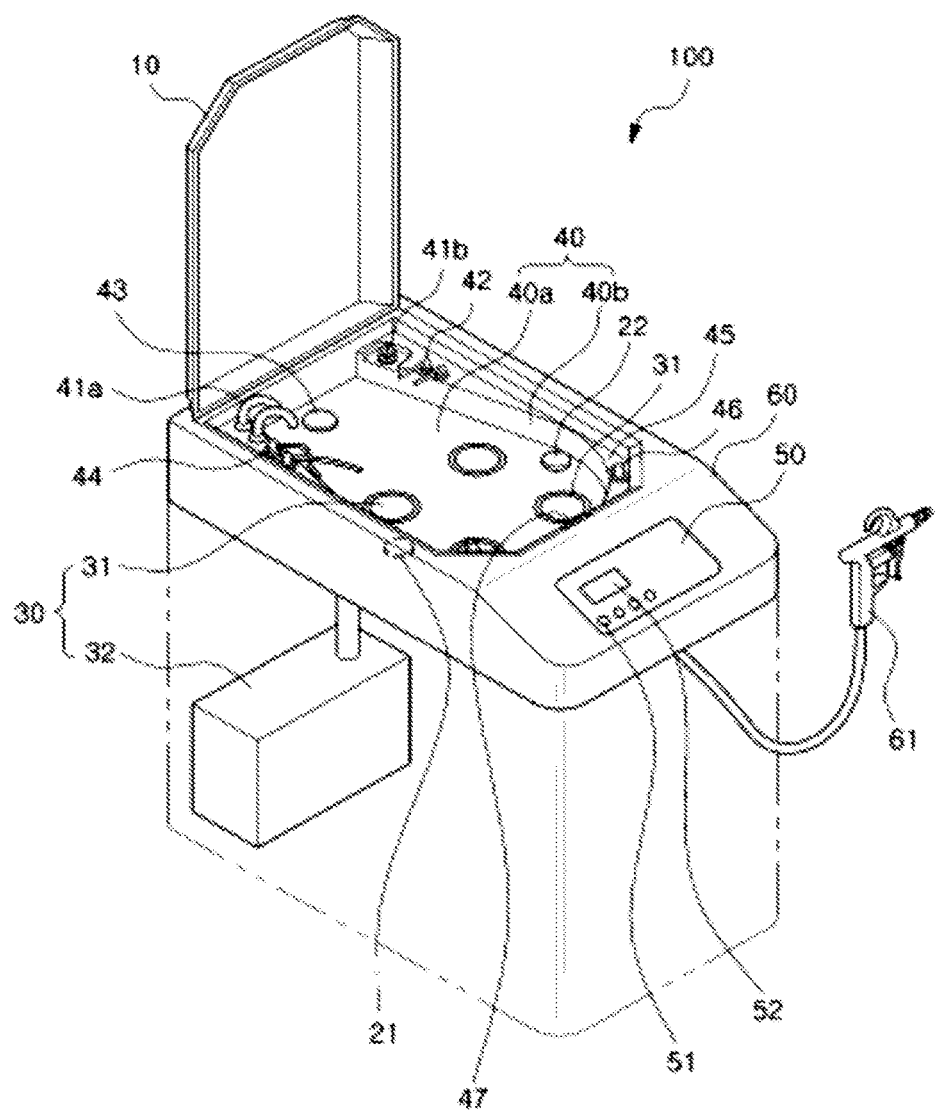
FIG. 1 is a perspective view illustrating the appearance of an apparatus for sterilizing a medical container according to one embodiment of the present invention.
Figure 2:
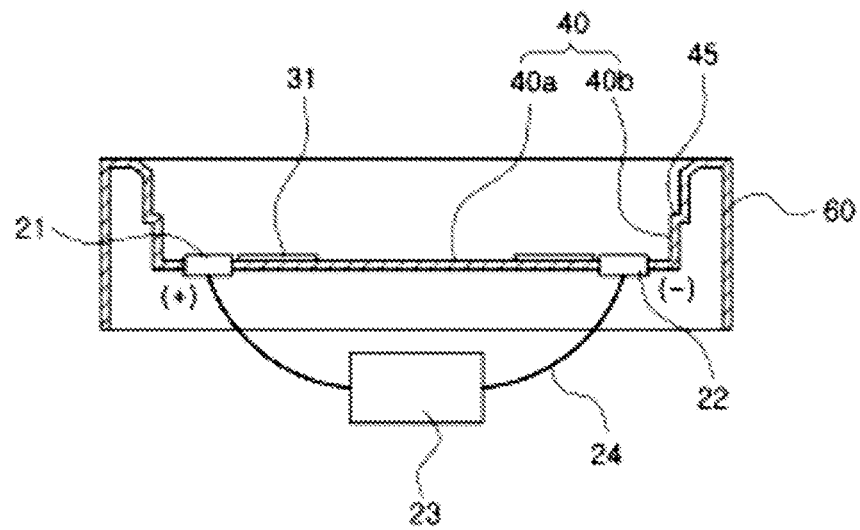
FIG. 2 is an enlarged side view illustrating essential parts of the apparatus of FIG. 1.

FIG. 1 is a perspective view illustrating the appearance of an apparatus 100 for sterilizing/cleaning a medical appliance according to one embodiment of the present invention and explains how the present invention is applied to a conventional apparatus for sterilizing/cleaning a medical appliance. FIG. 2 illustrates an essential construction of the apparatus of FIG. 1 in which two electrode rods 21 and 22 are arranged at both sides of the bottom surface of a sterilization/cleaning tank 40, one 21 of the electrode rods is connected to a positive (+) electrode, the other electrode rod 22 is connected to a negative (−) electrode, and a field effect transistor 23 is connected to the electrode rods 21 and 22 through 2.0 to 5.0 mm thick electric wires 24.

In the apparatus 100 illustrated in FIG. 1, the bottom surface 40a of the sterilization/cleaning tank 40 together with a side wall 40b defines a cleaning space. A medical appliance as an object to be sterilized/cleaned is accommodated in the sterilization/cleaning tank 40. A cover 10 is openably and closably coupled to the sterilization/cleaning tank 40. The electrode rod 21 connected to the positive (+) electrode and the electrode rod 22 connected to the negative (−) electrode are arranged at both sides of the bottom surface 40a. With this arrangement, the medical appliance can be sterilized/cleaned. The apparatus 100 includes an ultrasonic cleaning unit 30 including an ultrasonic oscillator 32 mounted below the sterilization/cleaning tank 40 and a plurality of ultrasonic transducers 31 formed on the bottom surface 40a. The ultrasonic oscillator 32 operates such that the ultrasonic transducers 31 are vibrated to clean the medical appliance. The apparatus 100 includes a control unit 50 and a body 60. The control unit 50 controls the apparatus 100. The body includes an air dry gun 61 arranged at one side of the sterilization/cleaning apparatus 100.

The apparatus of the present invention includes water supply valves 41a and 41b through which cleaning water is supplied to the cleaning space. The apparatus of the present invention may optionally further include valves 42 through which a cleaning solvent, such as alcohol, is supplied. A discharge hole 43 is formed at the bottom of the cleaning space and sensors 44 are mounted in front of one side of the cleaning space such that signals corresponding to the opening/closing state of the cover 10 are transmitted to the control unit 60. When the cover 10 is in an open position, the apparatus 100 is turned off. Only when the cover 10 is in a closed position is the apparatus 100 turned on. The sterilization/cleaning tank 40 accommodates a medical appliance as an object to be sterilized/cleaned and the cover 10 is openably and closably coupled to the sterilization/cleaning tank 40. Only when the cover 10 is in a closed position is the apparatus 100 turned on.

The water supply valves 41 are connected to a water supply tank mounted below the apparatus 100 to supply water to the cleaning space. The water supply valves 41 may be disposed around a protrusion 45 formed between the cleaning space and the body. The sterilization/cleaning tank has spray nozzles 46 through which a cleaning solution is sprayed on the surface of cleaning water filled therein. A water level sensor 47 is mounted on the bottom surface of the protrusion 45 protruding a predetermined height from the bottom surface of the sterilization/cleaning tank 40. When the amount of water supplied reaches a predetermined level, the operation of a water supply pump is stopped to block the supply of water.

The control unit 50 controls the apparatus 100 and has a plurality of operation buttons 51 and a display 52 such that cleaning and sterilization modes are selectively performed. The progress of the modes can be observed through the display 52 from the outside. The sterilization/cleaning modes can be selected through the operation buttons 51.

Since the features of the apparatus are not exactly visible from the perspective view of FIG. 1, essential parts of the apparatus are illustrated in FIG. 2 to explain how contaminants present in an object to be sterilized/cleaned are instantaneously removed by the apparatus. As illustrated in FIG. 2, the electrode rods 21 and 22 slightly protrude from the bottom surface of the sterilization/cleaning tank 40 and are connected to positive (+) and negative (−) electrodes, respectively. This connection enables instantaneous sterilization of water present in the sterilization/cleaning tank by electrical energy. The electrode rods are made of a conductive metal selected from Pt, Au, Ag, Cu, Sn, and alloys thereof and are arranged to face each other on the bottom surface of the sterilization/cleaning tank. The electrode rod 21 connected to the positive (+) electrode and the electrode rod 22 connected to the negative (−) electrode are connected to the field effect transistor 23 interposed therebetween through the 2.0 to 5.0 mm thick electric wires 24. Due to this structure, when electric power is applied to the electrode rods, water in the sterilization/cleaning tank is instantaneously sterilized by electrical energy as physical means to instantaneously kill microbial bacteria. This sterilization is based on the ability of the field effect transistor to produce a large output from a small input and to send a high voltage to the 2.0 to 5.0 mm thick electric wires 24 at one time.

Although only two electrode rods 21 and 22 are illustrated in FIGS. 1 and 2, it should be understood that the number of the electrode rods may vary depending on the capacity or size of the sterilization/cleaning tank. For example, four or six electrode rods may be arranged to face each other.

Figure 3:
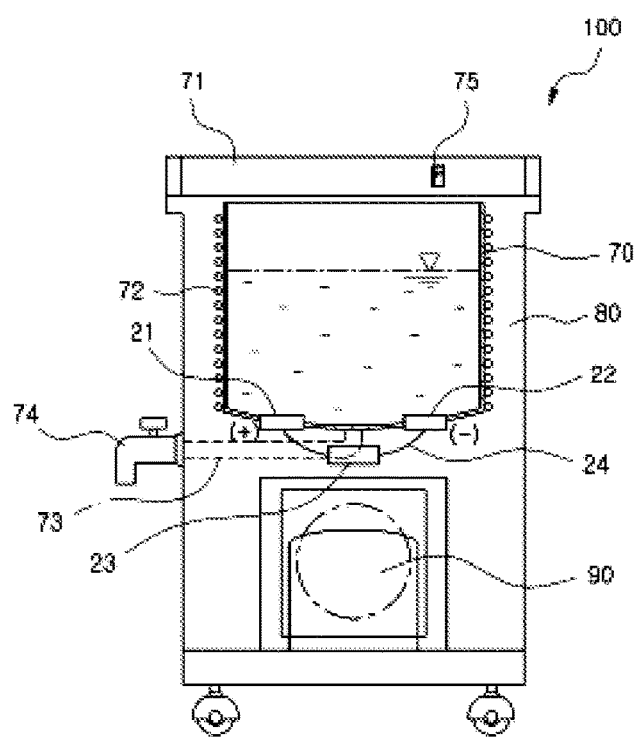
FIG. 3 illustrates an application example of a liquid food storage apparatus according to one embodiment of the present invention.

FIG. 3 illustrates an application example of an apparatus 110 for sterilizing a liquid food in a food storage container 70. The liquid food may be, for example, a meat broth for Korean traditional cold noodles, a Korean traditional sweet rice drink or a Korean traditional cinnamon punch made from dried persimmons. For example, a meat broth for Korean traditional cold noodles may be kept cool in the food storage container 70. To this end, the apparatus 110 includes a freezing compressor 90 and a cooling fan provided under an outer case body 80. The freezing compressor 90 and the cooling fan operate such that a liquified refrigerant passes through a refrigerant circulating tube 72 surrounding the food storage container 70 to cool the food storage container 70. The apparatus 110 includes a cover 71 on top of the food storage container 70. The cover 71 seals the food storage container 70 by packing. The apparatus 110 includes a discharge pipe 73 and a discharge valve 74 below the food storage container 70. The valve is openable/closable such that the liquid food is discharged as much as needed.

The apparatus 110 is structurally similar to that commonly used for the storage of a drink, such as a Korean traditional sweet rice drink or a fruit juice, or a food, such as a meat broth for Korean traditional cold noodles, in a store, and its detailed description is thus omitted. The essential parts of the apparatus illustrated in FIG. 2 are provided on the underside of the food storage container 70. As illustrated in FIG. 2, the slightly protruding electrode rods 21 and 22 connected to positive (+) and negative (−) electrodes, respectively, are connected to the field effect transistor 23 interposed therebetween through the 2.0 to 5.0 mm thick electric wires 24. Due to this structure, when electric power is applied to the electrode rods, water in the sterilization/cleaning tank is instantaneously sterilized by electrical energy. This sterilization is based on the ability of the field effect transistor 23 to produce a large output from a small input and to send a high voltage to the 2.0 to 5.0 mm thick electric wires 24 at one time. The electrode rods are made of a conductive metal selected from Pt, Au, Ag, Cu, Sn, and alloys thereof and are arranged to face each other on the bottom surface of the sterilization/cleaning tank. Based on the above construction and principle, the liquid food present in the food storage container 70 is instantaneously sterilized by electrical energy as physical means to instantaneously kill microbial bacteria.

In the apparatuses explained with reference to FIGS. 1 to 3, the conductive electrode rods are arranged at both sides of the bottom surface of the sterilization/cleaning tank or the liquid food storage container, one of the electrode rod is connected to a positive (+) electrode, the other electrode rod is connected to a negative (−) electrode, and the electrode rods at both sides are connected to the field effect transistor interposed therebetween through the 2.0 to 5.0 mm thick electric wires. When electric power is applied to the electrode rods, water in the tank or container is instantaneously sterilized by electrical energy to kill microbial bacteria. The same principle can be applied to a water container to sterilize the water. The sterilization apparatus or the liquid food storage apparatus may further include a sensor (not shown) for detecting the amount of electric current flowing between the electrode rods 21 and 22. The sensor is connected to the control unit 21. The voltage applied to the electrode rods can be controlled to 230-500 volts by the control unit in response to signals input from the sensor while visually observing through the digital display 52.

The sterilization apparatus or the liquid food storage apparatus is constructed such that when water stored in the apparatus or the container is used up or the body of the apparatus or container loses its balance to expose the electrode rods 21 and 22 from the water, no electric current flows between the electrode rods 21 and 22, which is detected by the current detection sensor. Preferably, the control unit receives signals detected by the current detection sensor to stop the operation of the related parts or the ultrasonic transducers, so that the electrical function of the apparatus can be stopped. After the operation of the apparatus is stopped, the shortage of water or the disconnection state of the apparatus is displayed through display means of LED display lamps 75 or the digital display 52 or is delivered as voice.

A request was filed in the name of KO Hwa-ok, the representative director of Lijin Co., Ltd. for which the present inventor is currently working, with the Institute for Health and Environment, Gyeonsangnamdo, Korea, on Jul. 12, 2016 to confirm whether sterilized water obtained from the apparatus to which the principles of the electrode rods and the field effect transistor illustrated in FIG. 2 are applied meets the test requirements for drinkable water. According to the results received on Jul. 19, 2016, the sterilized water met all of the requirements. FIG. 4 shows the analytical report of the water obtained from the apparatus.

As is apparent from the above description, the sterilization apparatus or the liquid food storage apparatus of the present invention instantaneously kills microbial bacteria by simple electrical energy as physical means. Although the sterilization apparatus and the liquid food storage apparatus have been described with reference to the foregoing embodiments, those skilled in the art will appreciate that various changes or modifications may be made to these embodiments without departing from the spirit and scope of the invention.

What is claimed is:

1. An apparatus for sterilizing/cleaning a food or a medical appliance, comprising: a sterilization tank; electrode rods arranged to face each other at both sides of the bottom surface of the sterilization tank and made of a conductive metal selected from Pt, Au, Ag, Cu, Sn, and alloys thereof, the electrode rod at one side being connected to a positive (+) electrode and the electrode rod at the other side being connected to a negative (−) electrode; and a field effect transistor connected to the electrode rods through 2.0 to 5.0 mm thick electric wires, wherein when electric power is applied to the electrode rods, an object to be sterilized in the sterilization/cleaning tank is instantaneously sterilized by electrical energy.

2. The apparatus according to claim 1, wherein the field effect transistor is selected from IGBT and MOSFET systems.

3. The apparatus according to claim 1, further comprising a sensor mounted in a connection unit of the apparatus or on the surface of the apparatus and a control unit adapted to interrupt the internal power of the apparatus when an external force is applied to disconnect the connection unit or an external object approaches the surface of the apparatus.

4. A method of using an apparatus for sterilizing a food or a medical appliance, the method comprising: constructing a sterilization apparatus in which electrode rods made of a conductive metal selected from Pt, Au, Ag, Cu, Sn, and alloys thereof are arranged to face each other at both sides of the bottom surface of a sterilization tank, the electrode rod at one side is connected to a positive (+) electrode, the electrode rod at the other side is connected to a negative (−) electrode, and a field effect transistor is connected to the electrode rods through 2.0 to 5.0 mm thick electric wires (step 1); and placing an object in need of sterilization in the sterilization tank and applying electric power to the electrode rods such that the object is instantaneously sterilized by electrical energy (step 2).

5. The method according to claim 4, wherein, in step 2, water is placed in the sterilization tank instead of the object to be sterilized and electric power is applied to sterilize the water, which is used to sterilize a food or a medical appliance.

6. The method according to claim 4, wherein sterilization apparatus is applied to the sterilization of a meat broth for Korean traditional cold noodles or a soup for Korean traditional bean noodles.

* * * * *